(12) United States Patent
Wei et al.

(10) Patent No.: US 8,361,515 B2
(45) Date of Patent: Jan. 29, 2013

(54) **EXTRACTS OF *CHENOPODIUM AMBROSIOIDES* L., THE COMPOSITIONS COMPRISING SAID EXTRACTS, THE PREPARING PROCESS AND APPLICATION THEREOF**

(75) Inventors: Feng Wei, Tianjin (CN); Zhengliang Ye, Tianjin (CN); Jun Gao, Tianjin (CN); Chongnian Luo, Tianjin (CN); Dekun Li, Tianjin (CN); Jianming Chen, Tianjin (CN); Yonghong Zhu, Tianjin (CN); Junfeng Xiong, Tianjin (CN); Xiaoli Zheng, Tianjin (CN); Guangming Zhang, Tianjin (CN); Ying Zhao, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 248 days.

(21) Appl. No.: 12/159,609

(22) PCT Filed: Dec. 29, 2006

(86) PCT No.: PCT/CN2006/003691
§ 371 (c)(1),
(2), (4) Date: Dec. 23, 2008

(87) PCT Pub. No.: WO2007/076699
PCT Pub. Date: Jul. 12, 2007

(65) Prior Publication Data
US 2009/0130203 A1 May 21, 2009

(30) Foreign Application Priority Data

Dec. 31, 2005 (CN) .......................... 2005 1 0135358
Dec. 31, 2005 (CN) .......................... 2005 1 0135359
Oct. 30, 2006 (CN) .......................... 2006 1 0136500

(51) Int. Cl.
*A61K 36/00* (2006.01)
*A61K 9/64* (2006.01)
(52) U.S. Cl. ...................................... 424/725; 424/456
(58) Field of Classification Search .................. None
See application file for complete search history.

(56) References Cited

U.S. PATENT DOCUMENTS

| 5,039,699 | A | * | 8/1991 | Kurihara et al. | 514/458 |
| 5,696,169 | A | * | 12/1997 | Otsu et al. | 514/675 |
| 6,344,219 | B1 | * | 2/2002 | Zhang et al. | 424/725 |
| 2005/0013885 | A1 | * | 1/2005 | Chiasson | 424/764 |
| 2005/0113371 | A1 | * | 5/2005 | Ishiduka et al. | 514/231.2 |

FOREIGN PATENT DOCUMENTS

| CN | 1131556 A | 9/1996 |
| CN | 1506118 A | 6/2004 |
| CN | 2005/10135358.6 | 2/2010 |
| CN | 2006/10136500.3 | 3/2010 |
| CN | 2005/10135358.6 | 10/2010 |
| CN | 2006/10136500.3 | 11/2010 |
| CN | 2005/10135358.6 | 3/2011 |
| EP | 0 815 868 A1 | 1/1998 |
| EP | 06840721.2 | 6/2009 |
| EP | 06840721.2 | 9/2010 |
| EP | 06840721.2 | 2/2011 |
| KR | 2008-7018649 | 2/2011 |
| KR | 2008-7018649 | 11/2011 |
| MY | PI 20082118 | 5/2011 |
| RU | 2008130841/15 | 10/2010 |

OTHER PUBLICATIONS

Kishore et al, Antidermatophytic action of the essential oil of *Chenopodium ambrosioides* and an ointment prepared from it. Phytotherapy Research. 10: 453-455, 1996.*
Warren et al., "Unidentified Curved Bacillion Gastric Epithelium in Active Chronic Gastritis," Lancet, pp. 1273-1275, 1983.
Xu, Ling, Journal of First Military Medical University, 1995, 15(4):360-361.
Liu, Junying; Ma, Cailian, Journal of Practical Medical Techniques, 1998, 5(7):542-544.
Recent Developments in Science & Technology Abroad, 2003, (4):44-45.
Van der Hulst RWM, Chinese Journal of Digestion, 1995, 15(3):164-166.
Huang, Xuerui; Chang, Heling, Northwest Pharmaceutical Journal, 1998, 13(1):33-34.
Chen, Zhenmin, Liaoning Journal of Traditional Chinese Medicine, 1995, 22(10):472.
International Search Report for PCT/CN2006/003691 dated Apr. 5, 2007 and English Translation, 8 pages.
Huang et al., "Study on Chemical Constituents of Volatile Oil from *Chenopodium ambrosioides* L.", Journal of China Pharmaceutical University, (ISSN:1000-5048), 33(3), pp. 256-257, 2002 (Chinese).
Xiong et al., "Studies on the Chemical Constituents of the Volatile Oil From *Chenopodium ambrosioides* L. Grown in Hubei," Journal of Wuhan Botanical Research, (ISSN:1000-470X), 17(3), pp. 244-248, 1999 (Chinese).
Wang et al., "Studies on Anti-gastric Ulcer Action of Zhonghuaweikang in Rats Mice and Inhibitor Effect on *Helicobacter pylori*," Strait Pharmaceutical Journal, (ISSN:1006-3765), 11(2), pp. 16-19, 1999 (Chinese).
Cavalli et al., "Combined Analysis of the Essential Oil of *Chenopodium ambrosioides* by GC, GC-MS and $^{13}$C-NMR Spectroscopy; Quantitative Determination of Ascaridole, a Heat-sensitive Compound," Phytochemical Analysis, 15, pp. 275-279, (2004).
Wang et al., "Screening of anti-*Helicobacter pylori* herbs deriving from Taiwanese folk medicinal plants," FEMS Immunology and Medical Microbiology, 43, pp. 295-300, (2005).
Sagrero-Nieves et al., "Volatile Constituents from the Leaves of *Chenopodium ambrosioides* L.", J. Essent. Oil Res., 7:2, pp. 221-223, (1995).
Yang et al., "Antioxidant Capacity and Components of Essential Oil from the Fruit of *Chenopodium ambrosioides* L.", Chinese Journal of Spectroscopy Labatory, vol. 27, No. 5, pp. 1760-1763, (2010).

* cited by examiner

*Primary Examiner* — Qiuwen Mi
(74) *Attorney, Agent, or Firm* — Evan Law Group LLC

(57) ABSTRACT

The present invention relates to plant extracts, specifically, the extracts of Chinese medicine *Chenopodium ambrosioides* L. and the composition comprising thereof. The extracts of Chinese medicine *Chenopodium ambrosioides* L. are prepared by conventional methods for the extraction of volatile oil, and can be used to treat *Helicobacter Pylori*-induced diseases of digestive system, such as gastritis, gastric ulcer, etc., with easy availability of raw materials, simple preparations, prominent effects, and less side-effect.

20 Claims, 4 Drawing Sheets

Figure 1:
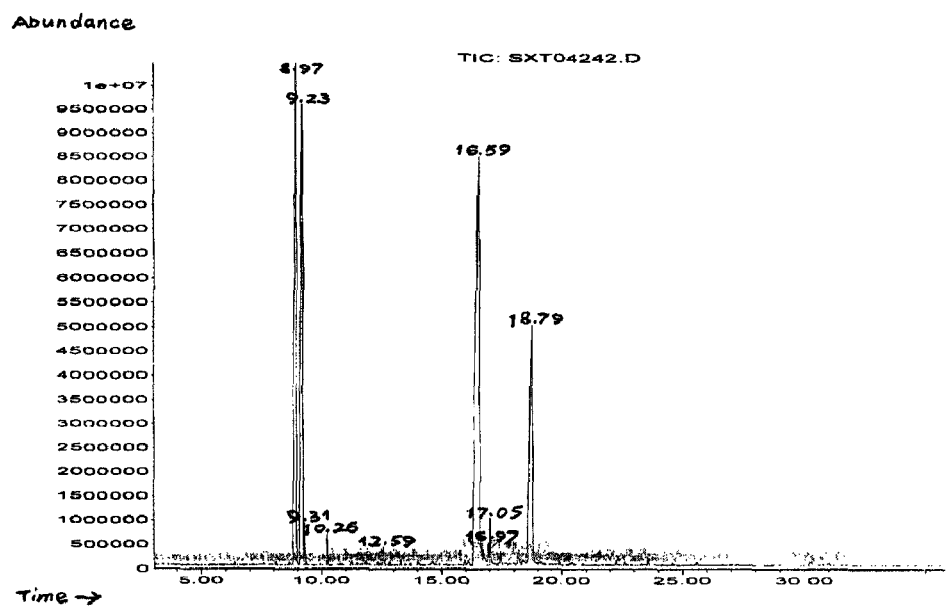

EXTRACTS OF *CHENOPODIUM AMBROSIOIDES* L., THE COMPOSITIONS COMPRISING SAID EXTRACTS, THE PREPARING PROCESS AND APPLICATION THEREOF

FIELD OF THE INVENTION

The present invention relates to a plant extracts, specifically, the extracts of Chinese medicine *Chenopodium ambrosioides L.*, preparations comprising said extracts and the preparing process thereof. The present invention also relates to the application of said extracts in the preparation of drugs for treatment of gastritis or gastric ulcer induced by *Helicobacter Pylori* (HP).

BACKGROUND OF THE INVENTIOIN

Gastric diseases are common and frequently-occurring diseases in clinic. Since it was reported by Marshall and Warren in *Lancet* in 1983 (Warren J R, Marshall B J. Lancet, 1983, 1:1273~1275.) that a kind of helical oxybiontic bacterial, which was named as *Helicobacter Pylori*, short for HP, was cultured on human gastric mucous membrane and was proved to be relevant to gastritis, a revolutionary change of recognition on upper respiratory tract illness has been triggered (Xu, Ling, Journal of First Military Medical University, 1995, 15(4):360-361.). With the deep research being carried out, it was gradually verified that the helical bacterial was the reason for causing various gastric diseases. For example, Liu et al proposed that the diseases related to HP infection included gastritis, gastric cancer, gastric lymphoma, duodenum diseases etc. (Liu, Junying; Ma, Cailian, Journal of Practical Medical Techniques, 1998, 5(7):542-544.). It was also reported that HP can induce various gastric diseases, for example, chronic gastritis, which can further cause gastric ulcer or gastratrophia, even developed to gastric cancer (Recent Developments in Science & Technology Abroad, 2003, (4):44-45.).

Based on the discovery mentioned above, people started to study drugs for treatment of HP, and at this time the combination of several chemical drugs are more frequently used in clinic. For example, 55 groups of pharmaceutical combinations used abroad were reviewed by Mo (Mo, Jianzhong, Chinese Journal of Digestion, 1995, 15(3):164.). Huang et al reported the combination of omeprazole and antibiotics (Huang, Xuerui; Chang, Heling, Northwest Pharmaceutical Journal, 1998, 13(1):33-34.). The compositions mentioned above are mainly the combination of proton pump inhibitors and antibacterial drugs, which can cause serious side effects, and antibiotics can easily induce drug resistance and dysbacteriosis.

Chinese medicine is famous for its slight side effects. Chinese medicine for treatment of HP are screened and shown that *Coptis chinensis Franch., Rheum officinale, Cortex Phellodendri., Herba Taraxaci, Polygonum cuspidatum Sieb. et Zucc., A. Sativam L.* var *Viviparum Regel, Ramulus Cinnamomi., Eugenia caryophyllata Thunb.* etc., are of high sensitivity (Chen, Zhenmin, Liaoning Journal of Traditional Chinese Medicine, 1995, 22(10):472.). *Chenopodium ambrosioides L.* is the whole herb of Chenopodiaceae plant *Chenopodium ambrosio des L.* with seed-bearing spike. Said whole herb contains 0.4-1% of volatile oil from *Chenopodium ambrosioides L.*, and the volatile oil comprises ascaridole, p-cymene and other terpenes such as aritasone and limonene etc. as main components; *Chenopodium ambrosioides L.* has functions of dispelling wind, anthelminthic action, clearing meridian and pain relief. So far, there are no reports about the effect of *Chenopodium ambrosioides L.* for treatment of gastritis and peptic gastric ulcer caused by HP.

DETAILED DESCRIPTION OF THE INVENTION

The main objective of the present invention is to overcome the deficiency of the drugs in the prior art and to provide extracts of *Chenopodium ambrosioides L.* with easy availability of raw materials, prominent effects, and less side-effects.

Another objective of the present invention is to provide compositions comprising said extracts.

Further objective of the present invention is to provide a method for preparing the extracts and compositions comprising said extracts.

The present invention also provides the application of said extracts and the compositions thereof in the preparation of drugs for treatment of gastritis and gastric ulcer induced by HP.

The term "extract of *Chenopodium ambrosioides L.*" used in the present invention is also named "volatile oil from *Chenopodium ambrosioides L.*".

The present invention is performed by the following technical solutions:

The extracts of *Chenopodium ambrosioides L.* of the present invention are analyzed by GC-MS, and the mass spectrum contains two peaks as follow:

Peak 1: retention time is 8.0-9.5 min, fragment ions m/e are 121 and 93; and

Peak 2: retention time is 9.0-10.0 min, fragment ions m/e are 120, 119 and 134;

Preferably, by GC-MS analysis, the mass spectrum further contains two peaks as follow:

Peak 3: retention time is 10.0-20.5 min, fragment ions m/e are 119, 121 and 136; and Peak 4: retention time is 15.0-20.5 min, fragment ions m/e are 135, 43 and 97.

More preferably, by GC-MS analysis, the mass spectrum further contains another two peaks as follow:

Peak 5: retention time is 5.5-15.5 min, fragment ions m/e are 93 and 91; and

Peak 6: retention time is 12.5-20.0 min, fragment ions m/e are 71, 126, 69 and 41.

The analytical conditions are as follows:

Preparation of samples: the extracts of *Chenopodium ambrosioides L.* are dissolved in ethyl acetate;

Gas chromatographic conditions:

Chromatographic column: HP-5MS 5% Phenyl Methyl Siloxane 60 m×0.25 mm×0.25 μm flexible silica capillary column;

Temperature programming: the temperature increases from 80° C. to 100° C., then increases to 150° C., and ends up to 300° C.

Vaporization temperature: 250° C.; Carrier gas: high-purity helium (99.999%); Flow rate of carrier gas: 1.0 mL/min; Injection volume of sample: 1 μL (ethyl acetate solution); Split ratio: 30:1;

Mass spectrum conditions:

Ion source: EI; Temperature of ion source: 230° C.; Temperature of quadrupole rods: 150° C.; Voltage of multiplier: 1781V; Temperature of interface: 280° C.; Scan range of mass: 10-550 amu.

The extracts of *Chenopodium ambrosioides L.* of the present invention comprise the following components by weight: α-terpinene 15-35% and p-cymene 15-25%.

Preferably, the extracts of *Chenopodium ambrosioides L.* of the present invention comprise the following components by weight: α-terpinene 15-35%, p-cymene 15-25%, ascaridole 10-20% and α-terpinolene 32-40%.

More preferably, the extracts of *Chenopodium ambrosioides L.* of the present invention comprise the following components by weight: α-terpinene 20-30%, p-cymene 18-22%, ascaridole 12-18% and α-terpinolene 32-35%.

Still more preferably, the extracts of *Chenopodium ambrosioides L.* of the present invention comprise the following components by weight: α-terpinene 22-25%, p-cymene 19-21%, ascaridole 13-15% and α-terpinolene 32-33%.

Further preferably, the extracts of *Chenopodium ambrosioides L.* of the present invention comprise the following components by weight: α-terpinene 15-35%, p-cymene 15-25%, ascaridole 10-20%, α-terpinolene 32-40%, γ-terpinene 0.5-0.7%, and limonene 0.6-0.8%;

or α-terpinene 15-35%, p-cymene 15-25%, ascaridole 10-20%, α-terpinolene 32-40%, and γ-terpinene 0.5-0.7%;

or α-terpinene 15-35%, p-cymene 15-25%, ascaridole 10-20%, α-terpinolene 32-40%, and limonene 0.6-0.8%;

Most preferably, the extracts of *Chenopodium ambrosioides L.* of the present invention comprise the following components by weight: α-terpinene 22-25%, p-cymene 19-21%, ascaridole 13-15%, α-terpinolene 32-33%, γ-terpinene 0.5-0.6%, and limonene 0.6-0.7%.

The present invention also provides pharmaceutical compositions comprising said extracts and pharmaceutically acceptable adjuvants.

The pharmaceutical compositions of the present invention can further comprise other active ingredient. For example, said active ingredient in the pharmaceutical compositions provided by the present invention is oil from Adina pilulifera (Lam.) Franch.

The pharmaceutical compositions provided by the present invention can be prepared into various pharmaceutical dosage forms. Said dosage forms include, but not limited to capsules, hard capsules, soft capsules (also referred to as gelatin pills), injections, drip solutions, injectable powders, granules, tablets, granules for infusion, powders, oral liquids, sugar-coated tablets, film-coated tablets, enteric coated tablets, buccal tablets, pills, ointments, pellets, spraying agent, drop pills, orally disintegration tablets, micro-pills, and aerosol etc.

Said capsules can be common capsules, or can be self-emulsifying preparation expressed in capsules form.

Preferably, the dosage form of the pharmaceutical composition comprising the extract of *Chenopodium ambrosioides L.* of the present invention as active ingredients is gelatin pill which consists of content and coating material. Said content of the gelatin pill is the extract of *Chenopodium ambrosioides L.* and vegetable oil.

Said vegetable oil is pharmaceutically acceptable, such as peanut oil, rapeseed oil, tea-seed oil, etc. in which solid fatty acid are removed.

The weight ratio of the extracts of *Chenopodium ambrosioides L.* to vegetable oil is 1:(1~3), preferably 1:(1~2); most preferably 1:1.

Said coating material of the gelatin pill includes gelatin and plasticizer, wherein the plasticizer is selected from a group consisting of glycerine, xylitol, sorbitol, and hydrogenated corn steep liquor; preferably, glycerine and xylitol; most preferably, glycerine.

Preferably, the dosage form comprising the extracts of *Chenopodium ambrosioides L.* of the present invention can be prepared into self-emulsifying preparations. The so-called self-emulsifying preparations are precursor of emulsions, and the self-emulsifying preparations are solid forms or homogeneous, transparent liquid forms comprising drug, oil phase, surfactant and cosurfactant. The basic characteristic of self-emulsifying preparations is that oil-in-water emulsions formed spontaneously in gastrointestinal tract (GIT) or under conditions of ambient temperature (usually refer to the body temperature 37° C.) and gentle agitation, the dissolution of the water-insoluble drugs in GIT is greatly improved by the increase of specific surface area of the fine oil droplets, therefore the bioavailability of drugs is increased significantly. Besides, the emulsions thus obtained can reduce GIT irritation of drugs. Self-emulsifying preparations can overcome the disadvantages of traditional preparations, such as instability, low-bioavailability, tedious preparation procedures, large doses, etc.

The weight ratio of components in the self-emulsifying preparation of the present invention is an extract of *Chenopodium ambrosioides L.* 1-95%, rapeseed salad oil 4-39%, surfactant 1-45%, and cosurfactant 0-15%, by weight; preferably, the weight ratio is an extract of *Chenopodium ambrosioides L.*, 20-70%, rapeseed salad oil 10-30%, surfactant 15-40%, and cosurfactant 5-10%.

Furthermore, the self-emulsifying preparation of the present invention can also comprise oil from Adina pilulifera (Lam.) Franch. The weight ratio of components in the preparation contains an extract of *Chenopodium ambrosioides L.* and oil from Adina pilulifera (Lam.) Franch. 1-95%, rapeseed salad oil 4-39%, surfactant 1-45%, and cosurfactant 0-15%; preferably, the weight ratio is an extract of Chenopodium ambrosioides L. and oil from Adina pilulifera (Lam.) Franch. 20-70%, rapeseed salad oil 10-30%, surfactant 15-40%, and cosurfactant 5-10%. And the weight ratio of an extract of *Chenopodium ambrosioides L.* to oil from Adina pilulifera (Lam.) Franch. is (1-5):1, preferably 3:1.

Said surfactant is selected from a group consisting of condensate of polyoxyethylene and castor oil, condensate of polyoxyethylene and hydrogenated castor oil, polysorbate, phospholipids, etc., or mixture thereof.

Said condensate of polyoxyethylene and castor oil is the condensate which has different number of polyoxyethylene linkage per molecule, for instance, polyoxyethylene (35) castor oil, polyoxyethylene (60) castor oil, etc. Said condensate of polyoxyethylene and hydrogenated castor oil is the condensate which has different number of polyoxyethylene linkage per molecule, for instance, polyoxyethylene (35) hydrogenated castor oil, polyoxyethylene (60) hydrogenated castor oil, etc. The preferred polysorbate is selected from, but not limited to polysorbate 60 and polysorbate 80. Said phospholipids include natural and synthesized phospholipids. Said natural phospholipids include yolk lecithin and soybean lecithin. Said synthesized phospholipids include, but not limited to, dipalmitoyl phosphatidylcholine, distearoyl phosphatidylcholine, dimyristoyl phosphatidylcholine, etc.

Said cosurfactant is selected from a group consisting of ethanol, glycol, propanediol, n-butanol, isopropanol, polyglycol 4000, and polyglycol 6000.

The present invention also provides a method for preparing pharmaceutical compositions containing extracts of *Chenopodium ambrosioides L.* according to following steps:
  a. Obtaining extracts of *Chenopodium ambrosioides L.* by conventional extraction method;
  b. Adding pharmaceutically acceptable adjuvants into the extracts to produce the desired preparations by conventional method.

The extract of *Chenopodium ambrosioides L.* can be prepared by conventional methods for extracting volatile oil, such as steam distillation, organic solvent soaking method (organic solvent refluxing method), simultaneous distillation-extraction (SDE), super critical carbon dioxide extraction, cold pressed method, etc.; preferably, steam distillation and super critical carbon dioxide extraction; and most preferably, steam distillation.

The optimal procedures of steam distillation are as follows: adding seeds or whole herbs of *Chenopodium ambrosioides L.* in distillatory kettle, applying steam to collector, keeping the extraction temperature at 85-100° C., distilling for a period of time, e.g. 40 minutes, and collecting the volatile oil from *Chenopodium ambrosioides L.*

The oil from Adina pilulifera (Lam.) Franch. can be prepared by conventional methods for extracting volatile oil, such as steam distillation, organic solvent soaking method (organic solvent refluxing method), simultaneous distillation-extraction (SDE), super critical carbon dioxide extraction, cold pressed method, etc.; preferably steam distillation and super critical carbon dioxide extraction; and most preferably steam distillation. The optimal procedures are as follows: adding stems and leaves of Adina pilulifera (Lam.) Franch. in distillatory kettle, applying steam to collector, keeping the extraction temperature at 85-100° C., distilling for a period of time, e.g. 40 minutes, and collecting the volatile oil.

Alternatively, *Chenopodium ambrosioides L.* and Adina pilulifera (Lam.) Franch. can be mixed and extracted by conventional methods for extracting volatile oil, such as steam distillation, organic solvent soaking method (organic solvent refluxing method), simultaneous distillation-extraction (SDE), super critical carbon dioxide extraction, cold pressed method etc.; preferably, steam distillation and super critical carbon dioxide extraction; more preferably, steam distillation. The optimal procedures of extraction method are as follows: adding seeds or whole herbs of *Chenopodium ambrosioides L.* and stems and leaves of Adina pilulifera (Lam.) Franch. in distillatory kettle, applying steam into collector, keeping the extraction temperature at 85-100° C., distilling for a period of time, e.g. 40 minutes, and collecting the volatile oil.

The method for preparing the compositions of the present invention, wherein the prepared compositions are gelatin pills, comprises the following steps: dissolving pharmaceutical gelatin and plasticizer in distilled water and filtering to get gelatin solution; solvating and diluting the volatile oil from *Chenopodium ambrosioides L.* with vegetable oil to give raw oil; adding the raw oil and the gelatin solution into the equipment for manufacturing gelatin pills to produce gelatin pills with oily liquid as content.

Said plasticizer is selected from a group consisting of glycerine, xylitol, sorbitol and hydrogenated corn steep liquor.

The method for preparing the composition of the present invention, wherein the prepared compositions are self-emulsifying preparations, comprises the following steps: mixing a prescribed dose of the volatile oil from *Chenopodium ambrosioides L.*, or the volatile oil from *Chenopodium ambrosioides L.* and oil from Adina pilulifera (Lam.) Franch., rapeseed salad oil, surfactants or further cosurfactant, heating the mixture by water bath at 30-80° C. or by ultrasonator to obtain homogenous and transparent solution, and then making them into soft or hard capsules preparations.

The surfactants used in the above-mentioned method for preparing said self-emulsifying preparations of the compositions can be selected from condensate of polyoxyethylene and castor oil, condensate of polyoxyethylene and hydrogenated castor oil, polysorbate, and phospholipid.

Further, said condensate of polyoxyethylene and castor oil is selected from polyoxyethylene (35) castor oil, polyoxyethylene (60) castor oil; said condensate of polyoxyethylene and hydrogenated castor oil is selected from polyoxyethylene (35) hydrogenated castor oil, and polyoxyethylene (60) hydrogenated castor oil; said polysorbate is selected from polysorbate 60 and polysorbate 80; said phospholipid is selected from yolk lecithin, soybean lecithin, dipalmitoyl phosphatidylcholine, distearoyl phosphatidylcholine, and dimyristoyl phosphatidylcholine. Said cosurfactant is selected from ethanol, glycol, propanediol, n-butanol, isopropanol, polyglycol 4000, and polyglycol 6000.

The extract of *Chenopodium ambrosioides L.* and the pharmaceutical composition comprising said extracts of the present invention can be used for treatment of gastric diseases caused by HP, such as gastritis, peptic ulcer, etc.

The present invention provides the active ingredient extracted from Chinese medicine *Chenopodium ambrosioides L.* for treatment of gastric diseases such as gastritis and peptic ulcer, etc. induced by HP, the raw materials are available easily, the preparing methods are simple and feasible, and quality-control is easy. Furthermore, the active ingredient has prominent effect, slight side effect and can be easily used. The self-emulsifying preparations further prepared are targeted preparations and can be absorbed more easily, thus bioavailability of the drugs increase. Meanwhile, the preparation can relieve adverse reaction of the patients, and the stability of drug is improved since the preparations can avoid the influence of unstable factors, e.g. water, oxygen, etc.

DESCRIPTIONS OF DRAWINGS

FIG. 1. Total ion-current spectrum of the volatile oil from Chenopodium ambrosioides L. from Fujian Province, China.

Figure 2:
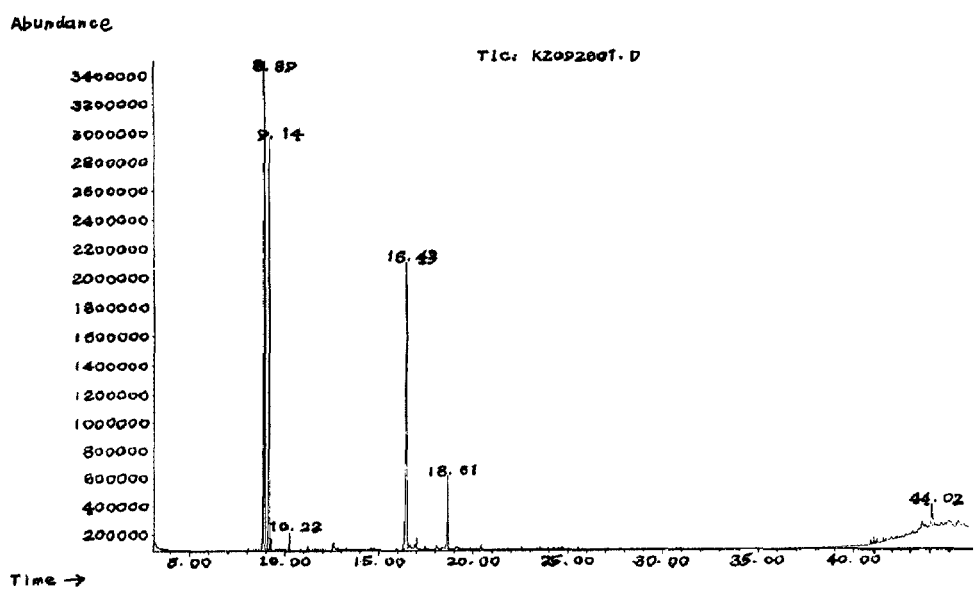

FIG. 2. Total ion-current spectrum of the volatile oil from Chenopodium ambrosioides L. from Hunan Province, China.

Figure 3:
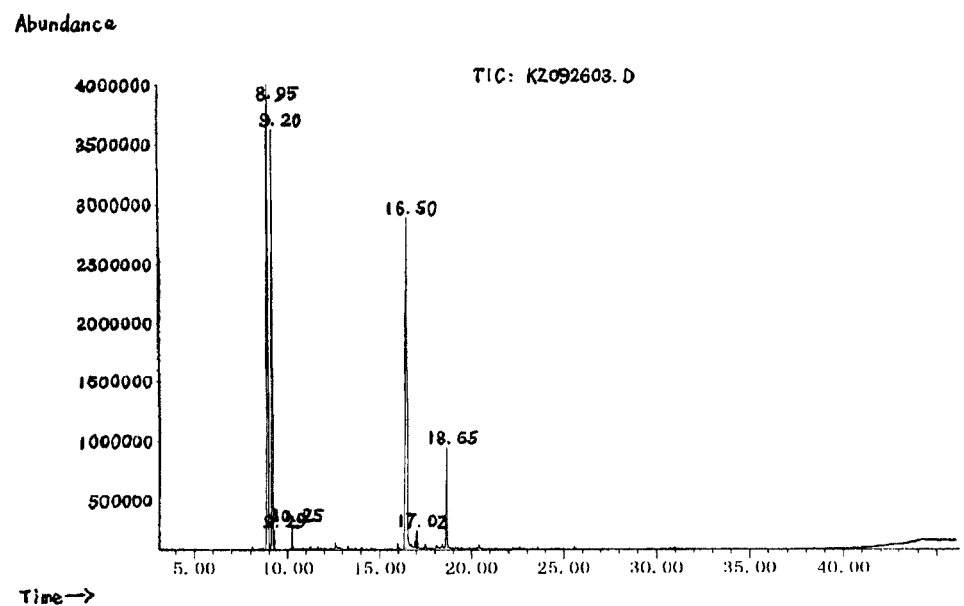

FIG. 3. Total ion-current spectrum of the volatile oil from Chenopodium ambrosioides L. from Shaanxi Province, China.

Figure 4:
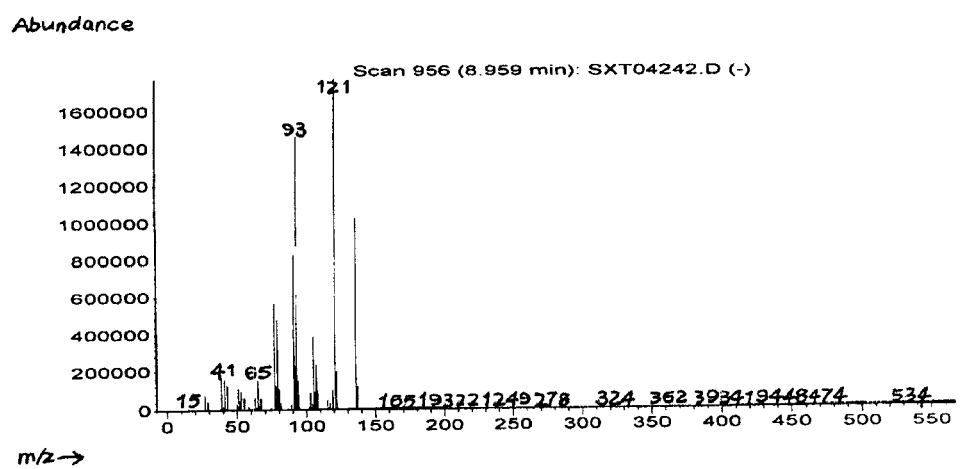

FIG. 4. Mass chromatogram of α-terpinene.

Figure 5:
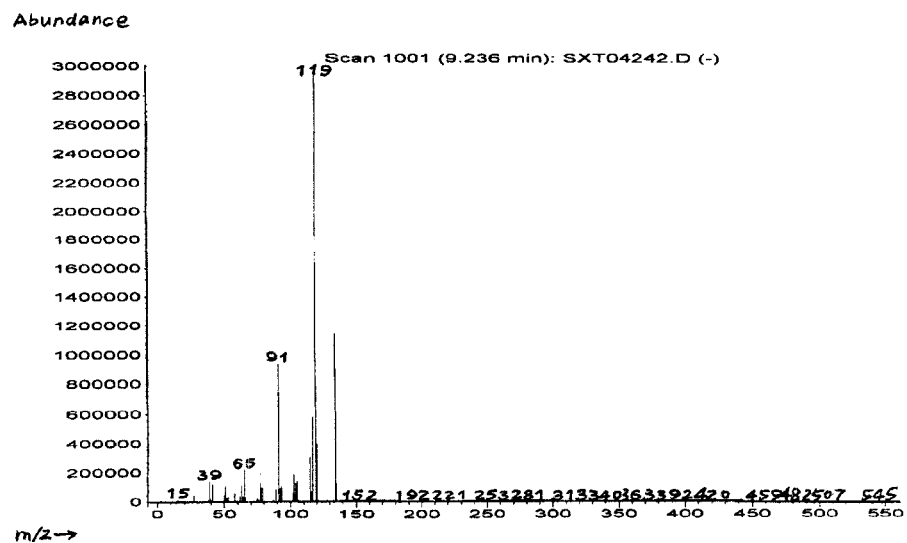

FIG. 5. Mass chromatogram of p-cymene.

Figure 6:
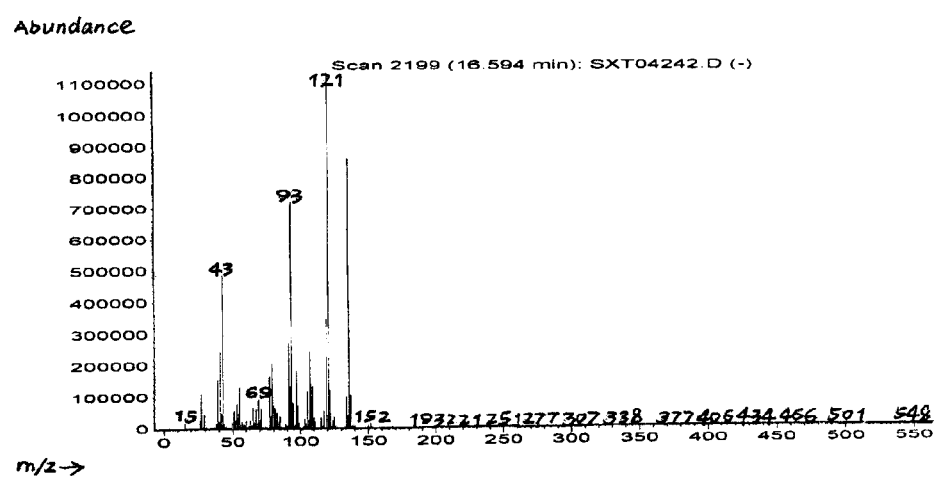

FIG. 6. Mass chromatogram of α-terpinolene.

Figure 7:
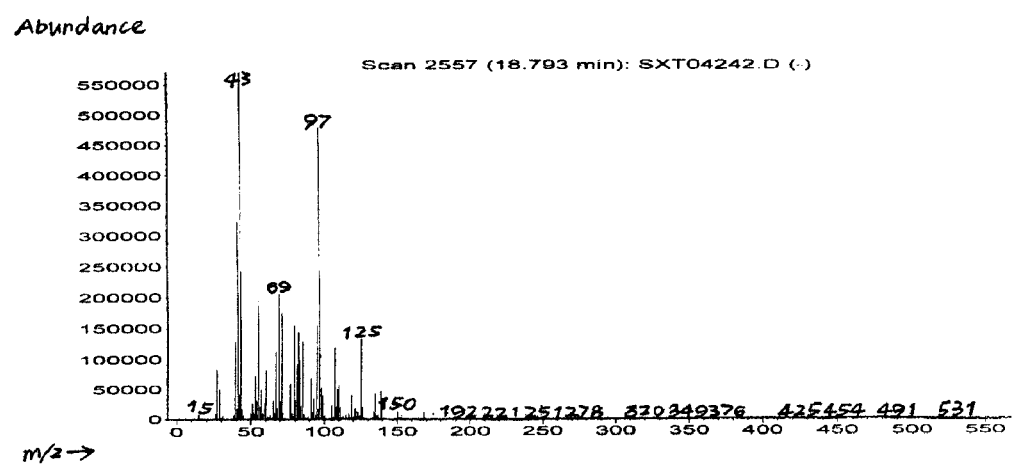

FIG. 7. Mass chromatogram of ascaridole.

The following experimental examples are given for further illustration of the present invention, but not for limiting the present invention in any way.

EXPERIMENTAL EXAMPLE 1

GC/MS analysis of the volatile oil from Chenopodium ambrosioides L.

1. Extraction of the Volatile Oil from *Chenopodium ambrosioides L.*
1.1. Medicinal Materials The medicinal materials are freshly collected Chenopodium ambrosioide L. from Fujian Province, China, which have been identified as plant of Chenopodiaceae, *Chenopodium, Chenopodium* ambrosio des L. by Quality Control Department, Tianjin Tasly Pharmaceutical Co., Ltd. *Chenopodium ambrosioides L.* from Hunan Province and Shaanxi Province are supplied by the medicinal materials planting bases of Tianjin Tasly Pharmaceutical Co., Ltd. in Hunan Province and Shaanxi Province.

1.2. Extraction Method 300 g of fresh whole herbs of *Chenopodium ambrosioides L.* were cut into small pieces and distilled by water vapor at normal pressure. Distillate was collected until no oil drops can be distilled out. Oil phase in the upper layer was separated and dried with anhydrous sodium sulphate, and about 2.2 mL of pale yellow volatile oil with special smell was obtained. Oil yield was about 0.75%.

2. Apparatus and Reagents 2.1. Apparatus

Gas chromatograph-mass spectrometer is HP6890/HP5973 gas chromatograph-mass spectrometer from Agilent Co., Ltd., U.S.

2.2 Reagents

Ethyl acetate (Analytical Pure, Tianjin No. 2 Chemical Reagent Factory); anhydrous sodium sulphate (Analytical Pure, Tianjin No. 2 Chemical Reagent Factory); De-ionized water (provided by Water Supply Plant of Tianjin Tasly Pharmaceutical Co., Ltd.).

3. Chromatographic Conditions 3.1 Gas Chromatographic Conditions

Chromatographic column: HP-5MS 5% Phenyl Methyl Siloxane 60 m×0.25 mm×0.25 μm flexible silica capillary column;

Temperature programming: the temperature begins from 80° C. and keeps at 80° C. for 10 min, and then increases to 100° C. with the rate of 4° C./min and keeps for 5min, increases to 150° C. with the rate of 5° C./min and keeps for 5 min, ends up at 300° C. with the rate of 20° C./min and keeps for 2.5 min.

Vaporization temperature: 250° C.; Carrier gas: high-purity helium (99.999%); Flow rate of carrier gas: 1.0 mL/min; Injection volume of sample: 1 μL (ethyl acetate solution); Split ratio: 30:1.

3.2. Mass Spectrum Conditions

Ion source: EI; Temperature of ion source: 230° C.; Temperature of quadrupole rods: 150° C.; Electron energy: 70 eV; Emission current: 34.6 μA; Voltage of multiplier: 1781V;

Temperature of interface: 280° C.; Scan range of mass: 10-550 amu.

4. Procedures 4.1 Qualitative Analysis

1 μL of ethyl acetate solution of the volatile oil from *Chenopodium ambrosioides L.* was injected and identified by GC-MS, and 70 chromatographic peaks were detected in the total ion chromatography (TIC) in which 33 components were identified by searching Nist98 standard MS library of HP MSD chemical station and referring to some relevant references.

4.2 The Ratio of each Component in the Volatile Oil

Based on Data Processing System of HP MSD chemical station, the relative percentage content of each component was calculated according to peak area normalization method.

5. Results

According to above-mentioned experimental conditions and procedures, TICs of the volatile oil from Fujian Province, Hunan Province and Shaanxi Province of China are shown in FIGS. 1-3, and the identified results of the common components are listed in Table 1.

TABLE 1

Identified results of the components in the volatile oil from *Chenopodium ambrosioides L.*

| Nos. | Compounds | Molecular Formulation | CAS | Chemical Structure | Relative Content (%) |
|---|---|---|---|---|---|
| 1 | 2-pinene | $C_{10}H_{16}$ | 80-56-8 | 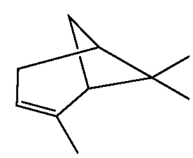 | 0.063% |
| 2 | pinene | $C_{10}H_{16}$ | 127-91-3 | 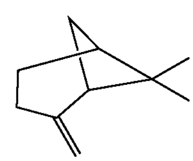 | 0.043% |
| 3 | myrcene | $C_{10}H_{16}$ | 123-35-3 | 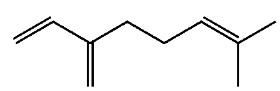 | 0.064% |
| 4 | 3-carene | $C_{10}H_{16}$ | 13466-78-9 | 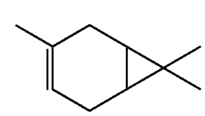 | 0.080% |
| 5 | α-terpinene | $C_{10}H_{16}$ | 99-86-5 | 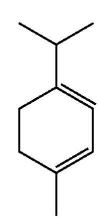 | 24.418% |

TABLE 1-continued

Identified results of the components in the volatile oil from *Chenopodium ambrosioides L.*

| Nos. | Compounds | Molecular Formulation | CAS | Chemical Structure | Relative Content (%) |
|---|---|---|---|---|---|
| 6 | p-cymene | $C_{10}H_{14}$ | 99-87-6 | 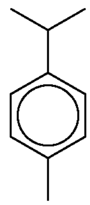 | 20.142% |
| 7 | (+)-(R)-limonene | $C_{10}H_{16}$ | 5989-27-5 | 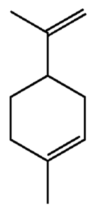 | 0.677% |
| 8 | γ-terpinene | $C_{10}H_{16}$ | 99-85-4 | 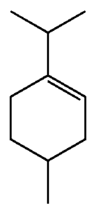 | 0.595% |
| 9 | p-isopropenyl toluene | $C_{10}H_{12}$ | 1195-32-0 | 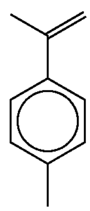 | 0.188% |
| 10 | 3,4-dimethylphenol, 6-ethyl- | $C_{10}H_{14}O$ | 2219-78-5 | 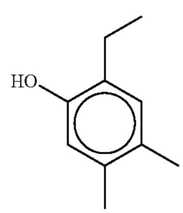 | 0.059% |
| 11 | cymene | $C_{10}H_{14}$ | 25155-15-1 | 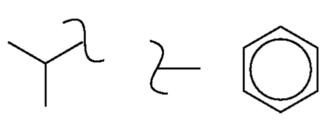 | 0.077% |
| 12 | 2-cyclohexen-1-ol, 1-methyl-4-(1-methyl-ethenyl)-, trans- | $C_{10}H_{16}O$ | 7212-40-0 | 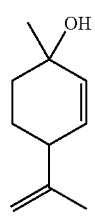 | 0.086% |

TABLE 1-continued

Identified results of the components in the volatile oil from *Chenopodium ambrosioides* L.

| Nos. | Compounds | Molecular Formulation | CAS | Chemical Structure | Relative Content (%) |
|---|---|---|---|---|---|
| 13 | cyclooctanone | $C_8H_{14}O$ | 502-49-8 | 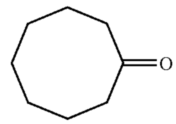 | 0.542% |
| 14 | 1,3,8-p-menthatriene | $C_{10}H_{14}$ | 21195-59-5 | 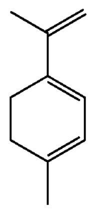 | 0.091% |
| 15 | cymene | $C_{10}H_{14}$ | 25155-15-1 | 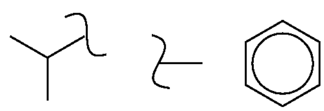 | 0.128% |
| 16 | durol | $C_{10}H_{14}$ | 95-93-2 | 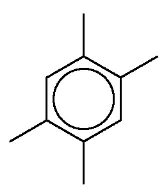 | 0.043% |
| 17 | cyclopentane, 1-methyl-2-acetyl-3-(1-methylethenyl)- | $C_{11}H_{18}O$ | 55757 | 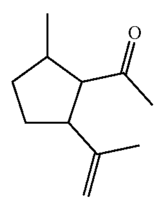 | 0.038% |
| 18 | trans-carveol | $C_{10}H_{16}O$ | 1197-07-5 | 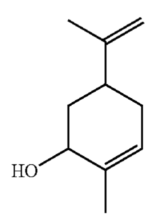 | 0.138% |
| 19 | 8-oxabicyclo[5.1.0]-oct-5-en-2-ol, 1,4,4-trimethyl- | $C_{10}H_{16}O_2$ | 58795-43-0 | 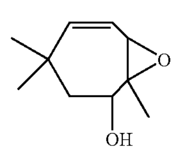 | 0.173% |
| 20 | terpinolene | $C_{10}H_{16}$ | 586-62-9 | 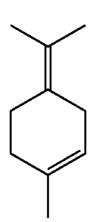 | 32.483% |

TABLE 1-continued

Identified results of the components in the volatile oil from *Chenopodium ambrosioides L.*

| Nos. | Compounds | Molecular Formulation | CAS | Chemical Structure | Relative Content (%) |
|---|---|---|---|---|---|
| 21 | 7-oxabicyclo[4.1.0]-heptan-2-one, 3-methyl-6-(1-methyl ethyl)- | $C_{10}H_{16}O_2$ | 5729-99-7 | 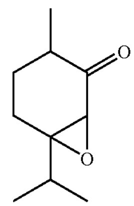 | 0.407% |
| 22 | p-menthan-3-one, 1,2-epoxy- | $C_{10}H_{16}O_2$ | 5286-38-4 | 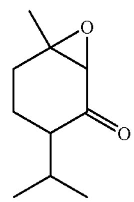 | 0.580% |
| 23 | m-thymol | $C_{10}H_{14}O$ | 89-83-8 | 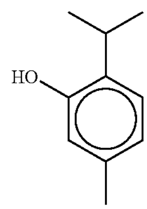 | 0.287% |
| 24 | ascaridole | $C_{10}H_{16}O_2$ | 512-85-6 | 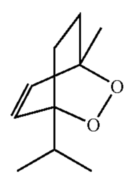 | 14.787% |
| 25 | perillaldehyde | $C_{10}H_{14}O$ | 2111-75-3 | 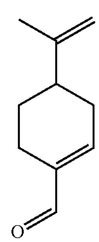 | 0.076% |
| 26 | 3-caren-10-al | $C_{10}H_{14}O$ | 151860 | 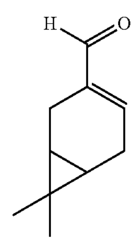 | 0.072% |
| 27 | caryophyllene | $C_{15}H_{24}$ | 87-44-5 | 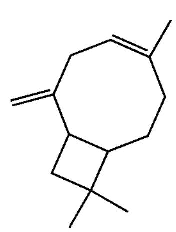 | 0.155% |

TABLE 1-continued

Identified results of the components in the volatile oil from *Chenopodium ambrosioides L.*

| Nos. | Compounds | Molecular Formulation | CAS | Chemical Structure | Relative Content (%) |
|------|-----------|----------------------|-----|---------------------|----------------------|
| 28 | isobutyl tiglate | $C_9H_{16}O_2$ | 61692-84-0 | 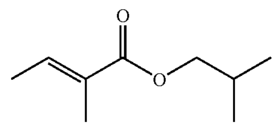 | 0.057% |
| 29 | precocene I | $C_{12}H_{14}O_2$ | 17598-02-6 | 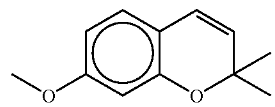 | 0.177% |
| 30 | β-cubebene | $C_{15}H_{24}$ | 13744-15-5 | 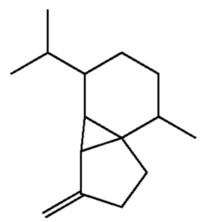 | 0.041% |
| 31 | m-menth-3(8)-ene | $C_{10}H_{18}$ | 13828-34-7 | 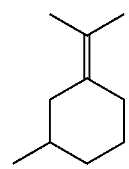 | 0.067% |
| 32 | 5-nonanol, 2,8-dimethyl- | $C_{11}H_{24}O$ | 19780-96-2 | 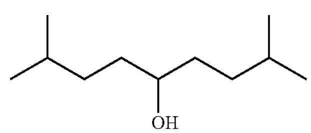 | 0.074% |
| 33 | precocene II | $C_{13}H_{16}O_3$ | 644-06-4 | 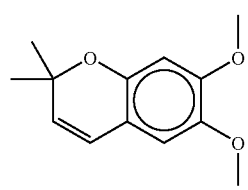 | 0.210% |

EXPERIMENTAL EXAMPLE 2

Pharmacodynamics Test of the Volatile Oil from *Chenopodium ambrosioides L.*

Experimental Materials
1. Tested Drug

The volatile oil from *Chenopodium ambrosioides L.*: yellow oily substance, was prepared according to the method of Example 5 (batch number: 20040129), supplied by Tianjin Tasly Pharmaceutical Co., Ltd., stored in sealed volumetric flask and diluted with vegetable oil to desired concentration before use for administering (i.g.) to animals.

2. Positive Control Drug

Ranitidine (batch number: 030836): purchased from Shijiazhuang No. 4 Pharmaceutical Co., Ltd.

3. Reagents 3.1 Vegetable oil: Fulinmen natural grain blending oil, market-available, batch number: 03110405.

3.2 Acetic acid: purchased from Tianjin Tianhe Chemical Reagent Factory, batch number: 20030722.

3.3 2% India ink: purchased from Beijing Xizhong Chemical Plant, batch number: 980301, and prepared with 5% arabic gum solution.

3.4 HP strain: International standard strain 26695.

3.5 Culture medium: Columbia agar base obtained from Oxoid, U.K.

3.6 Antibiotics: vancomycin hydrochloride, polymyxin B, amphotericin B, products of Sigma Company.

3.7 Mixed gas (5% $O_2$, 10% $CO_2$, 85% $N_2$): Beijing Pulaikesi Practical Gas Co., Ltd.

4. Experimental Animals 4.1. Km mice weighing between 18-22 g, male and female in half.

4.2. Wistar rats weighing between 160-220 g, male and female in half.

The experimental animals were provided by Animal Laboratory of Tianjin Institute of Pharmaceutical Research (certificate number: W-J Tianjin Experimental Animal Quality R Authorized No. 001)

All animals were housed in observation unit with central air conditioning (in accordance with standard of barrier level, Tianjin Experimental Facility Authorized No. 012). Mice and rats were fed with tap water and specific complete nutritious block feed, which was purchased from Tianjin Huarong Experimental Animal Technology Co., Ltd.

Methods and Results

1. Effect on Gastric Ulcer of Rats Induced by Acetic Acid Cautery

Eighty Wistar rats weighing between 200-220 g were selected in this experiment, male and female in half, and were randomly divided into 8 groups, 10 rats per group. Drugs were continually administered i.g. with the dosage listed in Table 2 for 13 days, once per day, while the model control group was administered i.g. with the same volume of vegetable oil. The model was established after 2 hours of the third administration. The rats were fasted for 24 hours before model-establishing and anaesthetized by ether, their abdomens were shaved and sterilized. A small incision was cut along the midline of the xiphoid. The stomach was gently pulled out, 10 μL 40% acetic acid was injected underneath the stomach chorion near pyloric gland areas. The stomach was then put back to the abdomen, and the incision was sewed up. Drugs were administered after operation. The rats were fasted for 24 hours after the last administration, and the animals were executed after being anaesthetized by urathane. The abdomen was cut open and the whole stomach was taken out and cut open along the greater curvature of stomach. After rinsing the content of stomach with saline, the stomach was fixed with 1% formaldehyde for 10 min, and then the diameters of ulcer points were measured using precise callipers and the ulcer areas were calculated. Ink was injected with a micro-syringe until its level reached the surface of gastric mucous membrane, and the volume of the injected ink was recorded. The degree of ulcer was expressed by the area of ulcer points and the volume of the injected ink. Results (see Table 2) showed that the ulcer area as well as the volume of injected ink decreased in the groups administered with the sample of volatile oil from *Chenopodium ambrosioides L.*, indicating that the drug has a significant effect on accelerating the healing of ulcer.

TABLE 2

Effect of the volatile oil from *Chenopodium ambrosioides L.* on acetic acid-cautery type gastric ulcer ($\overline{X} \pm SD$, n = 10)

| Groups | | Dosage (mg/kg) | Ulcer area (mm$^2$) | Volumes of injected ink in ulcer region (μL) |
| --- | --- | --- | --- | --- |
| Model control group | | — | 24.52 ± 11.29 | 7.74 ± 3.83 |
| Ranitidine | | 200 | 8.08 ± 5.72** | 2.85 ± 2.63** |
| Volatile oil from | High dosage | 20 | 10.57 ± 5.45** | 3.25 ± 1.24** |
| *Chenopodium ambrosioides L.* | Moderate dosage | 10 | 8.93 ± 6.64** | 2.27 ± 1.84** |
| | Low dosage | 5 | 8.71 ± 5.41** | 1.67 ± 1.29*** |

Compared with the model control group, *$p < 0.05$, $p < 0.01$, *$p < 0.001$.

2. Effect on Gastric Ulcers of Pyloric Ligation Type in Rats

Eighty Wistar rats weighing about 160 g were selected in this experiment, male and female in half, and were randomly divided into 8 groups, 10 rats per group. Drugs were continually administered i.g. with the dosage listed in Table 3 for 3 days, once per day, while the model control group was administered i.g. with the same volume of vegetable oil. The animals were anaesthetized by ether after 2 hours of the last administration (the rats were fasted for 48 hours before administration), and their abdomens were shaved and sterilized. A small incision was cut below the xiphoid. Their stomach was gently pulled out, and the stomach was then put back to the abdomen after pyloric ligation, and the incision was sewed up. After operation, the rats were abstained from food and water for 6 hours and executed after anaesthesia. The abdomen was cut open, the cardia was ligated, and the whole stomach was taken out and cut open along the greater curvature of stomach. After rinsing the content of stomach with saline, the stomach was fixed with 1% formaldehyde for 10 min, and then the diameters of the ulcer points were measured using precise callipers. Degree of the ulcer was expressed by total area of all ulcer points of each rat and was classified into 5 grades according to Okabe's method as index of ulcer. Results (see Table 3) showed that the indexes of ulcer of the drug groups were significantly lower than that of the model control group, indicating that the volatile oil from *Chenopodium ambrosioides L.* can significantly inhibit the formation of gastric ulcers of pyloric ligation type.

TABLE 3

Effect of the volatile oil from *Chenopodium ambrosioides L.* on gastric ulcers of pyloric ligation type ($\overline{X} \pm SD$, n = 10)

| Groups | | Dosage (mg/kg) | Index of Ulcer |
| --- | --- | --- | --- |
| Model control group | | — | 2.7 ± 1.8 |
| Ranitidine | | 200 | 0.8 ± 0.6** |
| Volatile oil from | High dosage | 20 | 0.9 ± 0.6* |
| *Chenopodium* | Moderate dosage | 10 | 1.0 ± 0.8* |
| *ambrosioides L.* | Low dosage | 5 | 0.9 ± 0.6* |

Compared with the model control group, *$p < 0.05$, **$p < 0.01$.
Note: Evaluation standard for the index of ulcer

| Index of ulcer | 1 | 2 | 3 | 4 | 5 |
| --- | --- | --- | --- | --- | --- |
| Ulcer area (mm$^2$) | 1-12 | 13-25 | 26-37 | 38-50 | ≥50 or gastric perforation |

With respect to the ulcer point which has an area smaller than 1 mm$^2$, the total area of ten such ulcer points is equal to 1 mm$^2$.

3. Effect on Intestinal Propulsive Movements in Mice

Eighty Km mice weighing between 18-22 g were selected in the experiment, female and male in half, and were randomly divided into groups, 10 mice per group. Drugs were continually administered i.g. with the dosage listed in Table 4 for 3 days, once per day, while the control group was administered i.g. with the same volume of vegetable oil. The animals of each group were administered i.g. with 2% Indian ink (prepared with 5% arabic gum solution) after 40 minutes of the last administration (the rats were fasted for 24 hours before administration), while the same volume of 5% arabic gum solution was administered to the control group. After 20 min, the mice were executed by cervical vertebra luxation. The abdomens were cut open, and the whole stomach and intestine were gently taken out, separated and laid on the wax board. The length from pylorus to ileocecal region was measured as the length of intestine. The length from pylorus to frontier of ink propulsion was measured as intestinal propulsion length. The ratio of the intestinal propulsion length to the whole length of intestine was used to calculate the propulsion percentage. T-test was carried out between mean values of propulsion percentage of each drug group and that of the control group. Results (see Table 4) showed that the intestinal propulsion percentages of the volatile oil from Chenopodium ambrosioides L. with high and moderate dosage are obviously lower than that of the control group, indicating that the drug has a significant inhibition on intestinal propulsive movement function.

TABLE 4

Effect of the volatile oil from *Chenopodium ambrosioides L.* on intestinal propulsion in mice ($\overline{X} \pm SD$, n = 10)

| Groups | | Dosage (mg/kg) | Percentage of ink propulsion ($\overline{X} \pm SD$ %) |
|---|---|---|---|
| Control group | | — | 49.25 ± 5.82 |
| Atropine | | 15 | 25.51 ± 10.92*** |
| Volatile oil from | High dosage | 20 | 32.73 ± 16.41* |
| *Chenopodium* | Moderate dosage | 10 | 31.30 ± 20.11* |
| *ambrosioides L.* | Low dosage | 5 | 30.47 ± 27.04 |

Compared with the control group, *p < 0.05, ***p < 0.001.

4. Test of Inhibitory Effect to *Helicobacter Pylori* in vitro

Bacterium strain: International standard bacterium strain 26695

Preparation of culture medium: 100 ml water was added into 3.9 g Columbia agar base, under high pressure of 15 pounds for 20 minutes. When cooled to 50° C., 7 ml of defibrinated sheep blood and 2 ml antibiotics were added under the sterile condition.

Conditions of mixed gas cultivation: the mixed gas of 5% $O_2$, 10% $CO_2$ and 85% $N_2$, with constant temperature at 37° C.

The drug was ground together with yolk, and the emulsified solution was obtained. After high pressure sterilization, the emulsified solution was serially diluted and was mixed with culture medium. 100 μL prepared bacterium solution was added into each culture dish and well spreaded. After culturing under slight anaerobic bacteria atmosphere at 37° C. for 72 hours, the results were observed. The lowest concentration of the volatile oil from *Chenopodium ambrosioides L.* in the culture dish without growing HP was considered to be the minimum inhibitory concentration. Results (see Table 5) showed that all the minimum inhibitory concentration of the volatile oil from *Chenopodium ambrosioides L.* was 0.097 mg/ml, indicating that the drug has a significant inhibitory effect on HP.

Conclusions

The above four experiments showed that the volatile oil from Chenopodium ambrosioides L. of the present invention has a significant accelerating effect on healing of acetic acid-cautery type gastric ulcer; a significantly inhibitory effect on the formation of gastric ulcers of pyloric ligation type; a significant inhibition on intestinal propulsive movement function; and a significant inhibition on the growth of HP in vitro.

EXAMPLES

The following examples are given for illustrating the scope of the present invention, but not for limiting the present invention in any way.

It is necessary to pointed out that the ratios in the following examples refer to weight ratios, and all portions mean weight portions.

Example 1

Preparation of Volatile Oil from *Chenopodium ambrosioides L.*

1000 g of whole herbs of *Chenopodium ambrosioides L.* were weighted and put into the extractor, the extraction temperature was adjusted at 35° C. and the pressure was 30 Mpa. The extraction was kept for 5 hours, with $CO_2$ flowing at 5 L/(kg medicine material * hour), and thus 5 g volatile oil was obtained by $CO_2$ super-critical extraction.

Example 2

Preparation of Volatile Oil from *Chenopodium ambrosioides L.*

1000 g of whole herbs of *Chenopodium ambrosioides L.* were weighted and put into the extractor, the extraction temperature was adjusted at 48° C. and the pressure was 30 Mpa. The extraction was kept for 8 hours, with $CO_2$ flowing at 7 L/(kg medicine material * hour), and thus 4.6 g volatile oil was obtained by $CO_2$ super-critical extraction.

Example 3

Preparation of Volatile Oil from *Chenopodium ambrosioides L.*

1000 g of whole herbs of *Chenopodium ambrosioides L.* were put into the distillatory kettle, applying steam to collec-

TABLE 5

Inhibitory effect of the volatile oil from *Chenopodium ambrosioides L.* on HP in vitro

| | Concentrations of drug (mg/ml) | | | | | | | | | | | | |
|---|---|---|---|---|---|---|---|---|---|---|---|---|---|
| Drug | 24.8 | 12.4 | 6.2 | 3.1 | 1.55 | 0.78 | 0.39 | 0.194 | 0.097 | 0.048 | 0.024 | 0.012 | 0 |
| Volatile oil from *Chenopodium ambrosioides L.* | | | | | | | | -- | -- | ++ | ++ | | ++ |

"++" means parallel samples, in which HP grows
"--" means parallel samples, in which the growth of HP is not observed.

tor, and the extraction temperature was kept at 85° C. After distilling for 40 min, 4.8 g volatile oil was collected.

Example 4

Preparation of Volatile Oil from *Chenopodium ambrosioides L.*

1000 g of whole herbs of *Chenopodium ambrosioides L.* were put into the distillatory kettle, applying steam to collector, and the extraction temperature was kept at 95° C. After distilling for 40 min, 5.2 g volatile oil was collected.

Example 5

Preparation of Volatile Oil from *Chenopodium ambrosioides L.*

1000 g of whole herbs of *Chenopodium ambrosioides L.* were put into the distillatory kettle, applying steam to collector, and the extraction temperature was kept at 90° C. After distilling for 40 min, 4.5 g volatile oil was collected.

Example 6

Preparation of Oil from Adina pilulifera (Lam.) Franch.

1000 g of stems and leaves of Adina pilulifera (Lam.) Franch. were put into the distillatory kettle, applying steam to collector, and the extraction temperature was kept at 95° C. After distilling for 40 min, 5.5 g volatile oil was collected.

Example 7

Preparation of Oil from Adina pilulifera (Lam.) Franch.

1000 g of stems and leaves of Adina pilulifera (Lam.) Franch. were put into the extractor, the extraction temperature was adjusted at 35° C. and the pressure was 30 Mpa. The extraction was kept for 4 hours, with $CO_2$ flowing at 5 L/(kg medicine material * hour), and thus 5.5 g volatile oil was obtained by $CO_2$ super-critical extraction.

Example 8

Preparation of Volatile Oil from *Chenopodium ambrosioides L.* and Oil from Adina pilulifera (Lam.) Franch.

600 g whole herbs of *Chenopodium ambrosioides L.* together with 400 g stems and leaves of Adina pilulifera (Lam.) Franch. were put into the extractor, the extraction temperature was adjusted at 35° C. and the pressure was 30 Mpa. The extraction was kept for 5 hours, with $CO_2$ flowing at 5 L/(kg medicine material hour), and thus 10.3 g volatile oil was obtained by $CO_2$ super-critical extraction.

Example 9

Preparation of Volatile Oil from *Chenopodium ambrosioides L.* and Oil from Adina piulifera (Lam.) Franch.

500 g whole herbs of *Chenopodium ambrosioides L.* together with 500 g stems and leaves of Adina pilulifera (Lam.) Franch. were put into the distillatory kettle, applying steam to collector, and the extraction temperature was kept at 85° C. After distilling for 40 min, 9.8 g volatile oil was collected.

Example 10

Preparation of Gelatin Pills 100 portions of gelatin were added into 120 portions of water, the mixture was swelled by absorbing water. Additional 30 portions of glycerine were heated to 60° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 1, and the weight ratio of the vegetable oil to the volatile oil from *Chenopodium ambrosioides L.* was 3:1; stirring well and obtaining the raw oil;

The above obtained gelatin solution together with the raw oil was put into auto rotary encapsulation machine, and were encapsulated to gelatin pills with 100 mg oily liquid per capsule as content. The gelatin pills were obtained after shaping, drying, washing, sterilizing, and packing.

Example 11

Preparation of Gelatin Pills 100 portions of gelatin were added into 140 portions of water, the mixture was swelled by absorbing water. Additional 30 portions of glycerine were heated to 70° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 2, and the weight ratio of the vegetable oil to the volatile oil from *Chenopodium ambrosioides L.* was 2:1; stirring well and obtaining the raw oil;

The above obtained gelatin solution together with the raw oil was put into auto rotary encapsulation machine, and were encapsulated to gelatin pills with 90 mg oily liquid per capsule as content. The gelatin pills were obtained after shaping, drying, washing, sterilizing, and packing.

Example 12

Preparation of Gelatin Pills 100 portions of gelatin were added into 130 portions of water, the mixture was swelled by absorbing water. Additional 30 portions of glycerine were heated to 80° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 3, and the weight ratio of the vegetable oil to the volatile oil from *Chenopodium ambrosioides L.* was 1.5:1; stirring well and obtaining the raw oil;

The above obtained gelatin solution together with the raw oil was put into drop pilling machine, and obtained gelatin pills with 90 mg oily liquid per capsule as content. The gelatin pills were obtained after shaping, drying, washing, sterilizing, and packing.

Example 13

Preparation of Gelatin Pills 100 portions of gelatin were added into 140 portions of water, the mixture was swelled by absorbing water. Additional 35 portions of glycerine were heated to 70° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 5, and the weight ratio of the vegetable oil to the volatile oil from *Chenopodium ambrosioides L.* was 1:1; stirring well and obtaining the raw oil;

The above obtained gelatin solution together with the raw oil was put into drop pilling machine, and obtained gelatin pills with 80 mg oily liquid per capsule as content. The gelatin pills were obtained after shaping, drying, washing, sterilizing, and packing.

Example 14

Preparation of Gelatin Pills 100 portions of gelatin were added into 120 portions of water, the mixture was swelled by absorbing water. Additional 40 portions of xylitol were heated to 80° C., and then the swelled gelatin was added into above xylitol, stirring, melting, and giving the gelatin solution, keeping it warm for use;

Vegetable oil was added into the volatile oil from *Chenopodium ambrosioides L.* prepared in Example 4, and the weight ratio of the vegetable oil to the volatile oil from *Chenopodium ambrosioides L.* was 1:1; stirring well and obtaining the raw oil;

The above obtained gelatin solution together with the raw oil was put into drop pilling machine, and obtained gelatin pills with 80 mg oily liquid per capsule as content. The gelatin pills were obtained after shaping, drying, washing, sterilizing, and packing.

Example 15

Preparation of Gelatin Pills 100 portions of gelatin were added into 120 portions of water, the mixture was swelled by absorbing water. Additional 30 portions of glycerine were heated to 60° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 5, and the weight ratio of the vegetable oil to the volatile oil from *Chenopodium ambrosioides L.* was 1.1:1; stirring well and obtaining the raw oil;

The above obtained gelatin solution together with the raw oil was put into drop pilling machine, and obtained gelatin pills with 80 mg oily liquid per capsule as content. The gelatin pills were obtained after shaping, drying, washing, sterilizing, and packing.

Example 16

Preparation of Gelatin Pills 100 portions of gelatin were added into 120 portions of water, the mixture was swelled by absorbing water. Additional 30 portions of sorbitol were heated to 80° C., and then the swelled gelatin was added into above sorbitol, stirring, melting, and giving the gelatin solution, keeping it warm for use;

Vegetable oil was added into the volatile oil from *Chenopodium ambrosioides L.* prepared in Example 5, and the weight ratio of the vegetable oil to the volatile oil from *Chenopodium ambrosioides L.* was 1.3:1; stirring well and obtaining the raw oil;

The above obtained gelatin solution together with the raw oil was put into soft capsule filling machine, and obtained gelatin pills with 80 mg oily liquid per capsule as content. The gelatin pills were obtained after shaping, drying, washing, sterilizing, and packing.

Example 17

Preparation of Gelatin Pills 100 portions of gelatin were added into 110 portions of water, the mixture was swelled by absorbing water. Additional 40 portions of hydrogenated corn steep liquor were heated to 80° C., and then the swelled gelatin was added into above hydrogenated corn steep liquor, stirring, melting, and giving the gelatin solution, keeping it warm for use;

Vegetable oil was added into the volatile oil from *Chenopodium ambrosioides L.* prepared in Example 5, and the weight ratio of the vegetable oil to the volatile oil from *Chenopodium ambrosioides L.* was 2.5:1; stirring well and obtaining the raw oil;

The above obtained gelatin solution together with the raw oil was put into rotary die encapsulation machine, and obtained gelatin pills with 90 mg oily liquid per capsule as content. The gelatin pills were obtained after shaping, drying, washing, sterilizing, and packing.

Example 18

Preparation of Gelatin Pills 100 portions of gelatin were added into 140 portions of water, the mixture was swelled by absorbing water. Additional 30 portions of glycerine were heated to 70° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 2, and the weight ratio of the vegetable oil to the volatile oil from *Chenopodium ambrosioides L.* was 1:1; and was sheared to suitable dispersivity by shearing dispersing emulsification machine and obtaining the raw oil;

The above obtained gelatin solution together with the raw oil was put into rotary die encapsulation machine, and obtained gelatin pills with 120 mg oily liquid per capsule as content. The gelatin pills were obtained after shaping, drying, washing, sterilizing, and packing.

Example 19

Preparation of Gelatin Pills 100 portions of gelatin were added into 120 portions of water, the mixture was swelled by absorbing water. Additional 30 portions of sorbitol were heated to 60° C., and then the swelled gelatin was added into above sorbitol, stirring, melting, and giving the gelatin solution, keeping it warm for use;

Vegetable oil was added into the volatile oil from *Chenopodium ambrosioides L.* prepared in Example 5, and the weight ratio of the vegetable oil to the volatile oil from *Chenopodium ambrosioides L.* was 2:1; and was sheared to suitable dispersivity by shearing dispersing emulsification machine and obtaining the raw oil;

The above obtained gelatin solution together with the raw oil was put into drop pilling machine, and obtained gelatin pills with 150 mg oily liquid per capsule as content. The gelatin pills were obtained after shaping, drying, washing, sterilizing, and packing.

Example 20

Preparation of Gelatin Pills 100 portions of gelatin were added into 130 portions of water, the mixture was swelled by absorbing water. Additional 30 portions of glycerine were heated to 70° C., and then the swelled gelatin was added into above glycerine, stirring, melting, and giving the gelatin solution, keeping it warm for use;

Vegetable oil was added into the volatile oil from *Chenopodium ambrosioides L.* prepared in Example 4, and the weight ratio of the vegetable oil to the volatile oil from *Chenopodium ambrosioides L.* was 2.5:1; and was sheared to suitable dispersivity by shearing dispersing emulsification machine and obtaining the raw oil;

The above obtained gelatin solution together with the raw oil was put into drop pilling machine, and obtained gelatin pills with 140 mg oily liquid per capsule as content. The gelatin pills were obtained after shaping, drying, washing, sterilizing, and packing.

Example 21

Preparation of Tablets 56 g of the volatile oil from *Chenopodium ambrosioides L.* prepared in Example 1 was mixed with starch in a ratio of 1:1, and 25 g sodium carboxymethycellulose was added to the above mixture and mixed well. 75% ethanol solution was added as adhesive, screened with 22 mesh sieve, dried in the oven at 40° C. An appropriate amount of magnesium stearate was added, tableting, to give tablets of 300 mg per tablet.

Example 22

Preparation of Coated Tablets 53 g of the volatile oil from *Chenopodium ambrosioides L.* prepared in Example 4 was mixed with 17 g light magnesium oxide, and 17 g starch and 17 g lactose were added. 0.5% HPMC aqueous solution was used as adhesive, to give plain tablets of 300 mg per tablet. Coated with 30% Eudragit RL30D, thus the coated tablets of 300 mg/tablet were obtained.

Example 23

Preparation of Capsules 52 g of the volatile oil from *Chenopodium ambrosioides L.* prepared in Example 3 was mixed with starch in a ratio of 1:1, and 25 g sodium carboxymethycellulose was added to the above mixture and mixed well. 75% ethanol solution was added as adhesive, screened with 22 mesh sieve, dried in the oven at 40° C., granulating, loading into the hard capsules to give the capsules of 270 mg/capsule.

Example 24

Preparation of Concentrated Pill 53 g of the volatile oil from *Chenopodium ambrosioides L.* prepared in Example 5 was mixed with microcrystalline cellulose, wherein the amount of microcrystalline cellulose accounts 40% of the volatile oil from *Chenopodium ambrosioides L.*, and water was added as adhesive to produce plain pill.

The above-mentioned plain pill was coated with coating materials, Opatry (stomach-soluble) from Shanghai Colorcon Coating Technology Co., Ltd., to give concentrated pills.

Coating conditions were as follows: water as solvent; the concentration of coating solution was 20%; coating weight increased by 5%; inlet air temperature was 80° C.; table bed temperature was 45° C.; spraying pressure was 2.0 bar; rotation speed of coating pan was 17 rmp ; Inlet flow rate was 3 g/min.

Example 25

Preparation of Granules 53 g of the volatile oil from *Chenopodium ambrosioides L.* prepared in Example 5, 9 g of methyl cellulose and 820 g of sugar powder were mixed well; an appropriate amount of 70% ethanol was added. The mixture was made into soft material, granulating, with ethanol volatilized; spray drying at 80° C., and thus the granules were obtained.

Example 26

Preparation of Drop Pills 300 g of polyglycol 6000 was heated to 80° C., and 50 g of the volatile oil from *Chenopodium ambrosioides L.* prepared in Example 3 was added after the polyglycol was melt, stirred well, and transferred to drop pilling machine. The temperature of melt solution being kept at 70° C., the solution was dropped from the top into methyl silicone oil at 10° C. in a moderate rate to produce drop pills.

Example 27

Preparation of Drop Pills 300 g of polyglycol 4000 was heated to 75° C., and 53 g of the volatile oil from *Chenopodium ambrosioides L.* prepared in Example 5 was added after the polyglycol was melt, stirred well, and transferred to drop pill machine. The temperature of melt solution being kept at 65° C., the solution was dropped from the top into liquid paraffin at 0° C. in a moderate rate to produce drop pills.

Example 28

Preparation of Drop Pills 300 g of polyglycol 4000 was heated to 90° C., and 60 g of the volatile oil from *Chenopodium ambrosioides L.* prepared in Example 1 was added after the polyglycol was melt, stirred well, and transferred to drop pill machine. The temperature of melt solution being kept at 80° C., the solution was dropped from the top into liquid paraffin at 4° C. in a moderate rate to produce drop pills.

Example 29

Preparation of Oral Liquid 500 g of the volatile oil from *Chenopodium ambrosioides L.* prepared in Example 5 was dissolved in an appropriate amount of ethanol, and 10 g glyceryl monostearate and 50 g sucrose were added and mixed well, then distilled water was added up to 1000 ml, filtering, sterilizing, packaging, to give the product.

Example 30

Preparation for Self-Emulsifying Soft Capsules of Chenopodium ambrosioides L. extract 100 portions of gelatin were added into 120 portions of water, the mixture was swelled by absorbing water. Additional 30 portions of glycerine were heated to 60° C., and then the swelled gelatin was added into above glycerine, stirring, melting, and giving the gelatin solution, keeping it warm for use;

10 g of the volatile oil from *Chenopodium ambrosioides L.* prepared in Example 1, 390 g of rapeseed salad oil, 500 g of polyoxyethylene (35) castor oil, and 100 g glycol were heated in water bath at 30° C. to give homogeneous and transparent solution, thus the raw drug was obtained;

The above obtained gelatin solution together with the raw oil was put into capsule machine, and obtained soft capsules with 100 mg oily liquid per capsule as content. The soft capsules were obtained after shaping, drying, washing, sterilizing, and packing.

Example 31

Preparation for Self-Emulsifying Soft Capsules of Chenopodium ambrosioides L. extract 100 portions of gelatin were added into 140 portions of water, the mixture was swelled by absorbing water. Additional 30 portions of glycerine were heated to 70° C., and then the swelled gelatin was added into above glycerine, stirring, melting, and giving the gelatin solution, keeping it warm for use;

200 g of the volatile oil from *Chenopodium ambrosioides L.* prepared in Example 1, 350 g of rapeseed salad oil, 250 g of polyoxyethylene (60) castor oil, and 200 g of soybean lecithin were mixed up by ultrasonator to give homogeneous and transparent solution at 50° C., thus the raw oil was obtained;

The above obtained gelatin solution together with the raw oil was put into capsule machine, and obtained soft capsules with 100 mg oily liquid per capsule as content. The soft capsules were obtained after shaping, drying, washing, sterilizing, and packing.

Example 32

Preparation for Self-Emulsifying Soft Capsules of Chenopodium ambrosioides L. extract 100 portions of gelatin were added into 120 portions of water, the mixture was swelled by absorbing water. Additional 30 portions of sorbitol were heated to 60° C., and then the swelled gelatin was added into above sorbitol, stirring, melting, and giving the gelatin solution, keeping it warm for use;

275 g of the volatile oil from *Chenopodium ambrosioides L.* prepared in Example 2, 325 g of rapeseed salad oil, 300 g of polyoxyethylene (60) castor oil, 50 g of yolk lecithin, and 50 g of propanediol were heated in water bath at 60° C. to give homogeneous and transparent solution, thus the raw drug was obtained;

The above obtained gelatin solution together with the raw oil was put into capsule machine, and obtained soft capsules with 150 mg oily liquid per capsule as content. The soft capsules were obtained after shaping, drying, washing, sterilizing, and packing.

Example 33

Preparation for Self-Emulsifying Soft Capsules of Chenopodium ambrosioides L. extract 100 portions of gelatin were added into 130 portions of water, the mixture was swelled by absorbing water. Additional 30 portions of sorbitol were heated to 80° C., and then the swelled gelatin was added into above sorbitol, stirring, melting, and giving the gelatin solution, keeping it warm for use;

600 g of the volatile oil from *Chenopodium ambrosioides L.* prepared in Example 3, 100 g of rapeseed salad oil, 50 g of polyoxyethylene (35) hydrogenated castor oil, 20 g of polysorbate 80, 80 g of distearoyl phosphatidylcholine, 30 g of dimyristoyl phosphatidylcholine, and 120 g of polyglycol 4000 were mixed up by ultrasonator to give homogeneous and transparent solution at 80° C., thus the raw oil was obtained;

The above obtained gelatin solution together with the raw oil was put into capsule machine, and obtained soft capsules with 120 mg oily liquid per capsule as content. The soft capsules were obtained after shaping, drying, washing, sterilizing, and packing.

Example 34

Preparation for Self-Emulsifying Soft Capsules of Chenopodium ambrosioides L. extract 100 portions of gelatin were added into 140 portions of water, the mixture was swelled by absorbing water. Additional 35 portions of glycerine were heated to 70° C., and then the swelled gelatin was added into above glycerine, stirring, melting, and giving the gelatin solution, keeping it warm for use;

735 g of the volatile oil from *Chenopodium ambrosioides L.* prepared in Example 3, 65 g of rapeseed salad oil, 50 g of polysorbate 60, 150 g of polyoxyethylene (60) hydrogenated castor oil were mixed up by ultrasonator to give homogeneous and transparent solution at 70° C., thus the raw oil was obtained;

The above obtained gelatin solution together with the raw oil was put into capsule machine, and obtained soft capsules with 150 mg oily liquid per capsule as content. The soft capsules were obtained after shaping, drying, washing, sterilizing, and packing.

Example 35

Preparation for Self-Emulsifying Hard Capsules of Chenopodium ambrosioides L. extract 950 g of the volatile oil from *Chenopodium ambrosioides L.* prepared in Example 2, 50 g of rapeseed salad oil, and 20 g of polyoxyethylene (35) hydrogenated castor oil were mixed up by ultrasonator to give homogeneous and transparent solution at 70° C., then the solution was filled to hard capsule shells and was encapsulated to capsules with 270 mg/capsule.

Example 36

Preparation for Self-Emulsifying Hard Capsules of Chenopodium ambrosioides L. extract 950 g of the volatile oil from *Chenopodium ambrosioides L.* prepared in Example 2, 40 g of rapeseed salad oil, 30 g of polyoxyethylene (60) hydrogenated castor oil, and 80 g of isopropanol were mixed up by ultrasonator to give homogeneous and transparent solution at 30° C., then the solution was filled to hard capsule shells and was encapsulated to capsules with 300 mg/capsule.

Example 37

Preparation for Self-Emulsifying Hard Capsules of Chenopodium ambrosioides L. extract 960 g of the volatile oil from *Chenopodium ambrosioides L.* prepared in Example 1, 40 g of rapeseed salad oil, and 15 g of polyoxyethylene (35) hydrogenated castor oil were mixed up by ultrasonator to give homogeneous and transparent solution at 70° C., then the solution was filled to hard capsule shells and was encapsulated to capsules with 200 mg/capsule.

Example 38

Preparation for Self-Emulsifying Hard Capsules of Chenopodium ambrosioides L. extract 335 g of the volatile oil from *Chenopodium ambrosioides L.* prepared in Example 5, 365 g of rapeseed salad oil, 150 g of polysorbate 80, and 150 g of of soybean lecithin were heated in water bath at 80° C. to give homogeneous and transparent solution, then the solution was filled to hard capsule shells and was encapsulated to capsules with 270 mg/capsule.

Example 39

Preparation for Self-Emulsifying Soft Capsules of Volatile Oil from *Chenopodium ambrosioides L.* and Oil from Adina pilulifera (Lam.) Franch.

100 portions of gelatin were added into 120 portions of water, the mixture was swelled by absorbing water. Additional 30 portions of sorbitol were heated to 80° C., and then the swelled gelatin was added into above sorbitol, stirring, melting, and giving the gelatin solution, keeping it warm for use;

450 g of the volatile oil from *Chenopodium ambrosioides L.* prepared in Example 1, 150 g of the oil from Adina pilulifera (Lam.) Franch. prepared in Example 6, 100 g of rapeseed salad oil, 50 g of polyoxyethylene (35) hydrogenated castor oil, 20 g of polysorbate 80, 80 g of distearoyl phosphatidylcholine, 30 g of dimyristoyl phosphatidylcholine, and 120 g of polyglycol 4000 were mixed up by ultrasonator to give homogeneous and transparent solution at 80° C., thus the raw oil was obtained;

The above obtained gelatin solution together with the raw oil was put into capsule machine, and obtained soft capsules with 120 mg oily liquid per capsule as content. The soft capsules were obtained after shaping, drying, washing, sterilizing, and packing.

Example 40

Preparation for Self-Emulsifying Soft Capsules of Volatile Oil from *Chenopodium ambrosioides L.* and Oil from Adina pilulifera (Lam.) Franch.

100 portions of gelatin were added into 140 portions of water, the mixture was swelled by absorbing water. Additional 35 portions of glycerine were heated to 70° C., and then the swelled gelatin was added into above glycerine, stirring, melting, and giving the gelatin solution, keeping it warm for use;

335 g of the volatile oil from *Chenopodium ambrosioides L.* prepared in Example 3, 365 g of the oil from Adina pilulifera (Lam.) Franch. prepared in Example 6, 100 g of rapeseed salad oil, 10 g of polyoxyethylene (60) hydrogenated castor oil, 20 g of polysorbate 80, 80 g of distearoyl phosphatidylcholine, and 120 g of polyglycol 4000 were mixed up by ultrasonator to give homogeneous and transparent solution at 60° C., thus the raw oil was obtained;

The above obtained gelatin solution together with the raw oil was put into capsule machine, and obtained soft capsules with 150 mg oily liquid per capsule as content. The soft capsules were obtained after shaping, drying, washing, sterilizing, and packing.

Example 41

Preparation for Self-Emulsifying Soft Capsules of Volatile Oil from *Chenopodium ambrosioides L.* and Oil from Adina pilulifera (Lam.) Franch.

100 portions of gelatin were added into 140 portions of water, the mixture was swelled by absorbing water. Additional 35 portions of glycerine were heated to 70° C., and then the swelled gelatin was added into above glycerine, stirring, melting, and giving the gelatin solution, keeping it warm for use;

490 g of the volatile oil from *Chenopodium ambrosioides L.* prepared in Example 2, 245 g of the oil from Adina pilulifera (Lam.) Franch. prepared in Example 7, 65 g of rapeseed salad oil, 50 g of polysorbate 60, and 150 g of polyoxyethylene (60) hydrogenated castor oil were mixed up by ultrasonator to give homogeneous and transparent solution at 70° C., thus the raw oil was obtained;

The above obtained gelatin solution together with the raw oil was put into capsule machine, and obtained soft capsules with 120 mg oily liquid per capsule as content. The soft capsules were obtained after shaping, drying, washing, sterilizing, and packing.

Example 42

Preparation for Self-Emulsifying Soft Capsules of Volatile Oil from *Chenopodium ambrosioides L.* and Oil from Adina pilulifera (Lam.) Franch.

100 portions of gelatin were added into 140 portions of water, the mixture was swelled by absorbing water. Additional 35 portions of glycerine were heated to 70° C., and then the swelled gelatin was added into above glycerine, stirring, melting, and giving the gelatin solution, keeping it warm for use;

735 g of the volatile oil from *Chenopodium ambrosioides L.* and the oil from Adina pilulifera (Lam.) Franch. prepared in Example 8, 65 g of rapeseed salad oil, 50 g of polysorbate 60, and 120 g of polyoxyethylene (60) hydrogenated castor oil were mixed up by ultrasonator to give homogeneous and transparent solution at 70° C., thus the raw oil was obtained;

The above obtained gelatin solution together with the raw oil was put into capsule machine, and obtained soft capsules with 100 mg oily liquid per capsule as content. The soft capsules were obtained after shaping, drying, washing, sterilizing, and packing.

Example 43

Preparation for Self-Emulsifying Hard Capsules of Volatile Oil from *Chenopodium ambrosioides L.* and Oil from Adina pilulifera (Lam.) Franch.

800 g of the volatile oil from *Chenopodium ambrosioides L.* prepared in Example 1, 150 g of the oil from Adina pilulifera (Lam.) Franch. prepared in Example 6, 40 g of rapeseed salad oil, and 10 g of polyoxyethylene (35) hydrogenated castor oil were mixed up by ultrasonator to give homogeneous and transparent solution at 70° C., then the solution was filled to hard capsule shells and was encapsulated to capsules with 200 mg/capsule.

Example 44

Preparation for Self-Emulsifying Hard Capsules of Volatile Oil from *Chenopodium ambrosioides L.* and Oil from Adina pilulifera (Lam.) Franch.

450 g of the volatile oil from *Chenopodium ambrosioides L.* prepared in Example 2, 150 g of the oil from Adina pilulifera (Lam.) Franch. prepared in Example 6, 100 g of rapeseed salad oil, and 10 g of polyoxyethylene (35) hydrogenated castor oil were mixed up by ultrasonator to give homogeneous and transparent solution at 50° C., then the solution was filled to hard capsule shells and was encapsulated to capsules with 270 mg/capsule.

Example 45

Preparation for Self-Emulsifying Hard Capsules of Volatile Oil from *Chenopodium ambrosioides L.* and Oil from Adina pilulifera (Lam.) Franch.

500 g of the volatile oil from *Chenopodium ambrosioides L*. and the oil from Adina pilulifera (Lam.) Franch. prepared in Example 9, 80 g of rapeseed salad oil, and 420 g of polyoxyethylene (60) hydrogenated castor oil were mixed up by ultrasonator to give homogeneous and transparent solution at 50° C., then the solution was filled to hard capsule shells and was encapsulated to capsules with 270 mg/capsule.

What is claimed is:

1. An essential oil extract from whole herbs including the seed-bearing spike of *Chenopodium ambrosioides L.*, wherein the extract comprises the following components by weight: α-terpinene 15-35%, p-cymene 15-25%, ascaridole 10-20% and α-terpinolene 32-40%.

2. The essential oil extract of *Chenopodium ambrosioides L.* according to claim 1, wherein the extract comprises the following components by weight: α-terpinene 20-30%, p-cymene 18-22%, ascaridole 12-18% and α-terpinolene 32-35%.

3. The essential oil extract of *Chenopodium ambrosioides L.* according to claim 2, wherein the extract further comprises the following components by weight: γ-terpinene 0.5-0.7%, and/or limonene 0.6-0.8%.

4. The essential oil extract of *Chenopodium ambrosioides L.* according to claim 1, wherein the extract further comprises the following components by weight: γ-terpinene 0.5-0.7%, and/or limonene 0.6-0.8%.

5. A pharmaceutical composition comprising
an essential oil extract from whole herbs including the seed-bearing spike of *Chenopodium ambrosioides L.*, wherein the extract comprises the following components by weight: α-terpinene 15-35%, p-cymene 15-25%, ascaridole 10-20% and α-terpinolene 32-40%, and
pharmaceutically acceptable adjuvants.

6. The pharmaceutical composition of claim 5, wherein the extract comprises the following components by weight: α-terpinene 20-30%, p-cymene 18-22%, ascaridole 12-18% and α-terpinolene 32-35%.

7. The pharmaceutical composition of claim 6, wherein the extract further comprises the following components by weight: γ-terpinene 0.5-0.7%, and/or limonene 0.6-0.8%.

8. The pharmaceutical composition of claim 5, wherein the extract further comprises the following components by weight: γ-terpinene 0.5-0.7%, and/or limonene 0.6-0.8%.

9. The pharmaceutical composition according to claim 5, wherein the composition is prepared into various dosage forms.

10. The pharmaceutical composition according to claim 9, wherein the dosage form is gelatin pills.

11. The pharmaceutical composition according to claim 10, wherein the weight ratio of the extract of *Chenopodium ambrosioides L.* to vegetable oil is 1:1-3, and said vegetable oil is used as the pharmaceutically acceptable carrier for solvating and diluting said extract.

12. The pharmaceutical composition according to claim 10, wherein the gelatin pills comprise a coating material, and the coating material includes gelatin and plasticizer, and the plasticizer is selected from the group consisting of glycerine, xylitol, sorbitol, and hydrogenated corn steep liquor.

13. The pharmaceutical composition according to claim 9, wherein the dosage forms is self-emulsifying preparations, and the weight ratio of the components is extract of *Chenopodium ambrosioides L.* 1-95%, rapeseed salad oil 4-39%, surfactant 1-45%, and cosurfactant 0-15%.

14. The pharmaceutical composition of claim 13, wherein the extract further comprises the following components by weight: γ-terpinene 0.5-0.7%, and/or limonene 0.6-0.8%.

15. The pharmaceutical composition according to claim 13, wherein the surfactant is selected from the group consisting of condensates of polyoxyethylene and castor oil, condensates of polyoxyethylene and hydrogenated castor oil, polysorbate, and phospholipids, and the cosurfactant is selected from the group consisting of ethanol, glycol, propanediol, n-butanol, isopropanol, polyglycol 4000, and polyglycol 6000.

16. The pharmaceutical composition according to claim 15, wherein the condensate of polyoxyethylene and castor oil is selected from polyoxyethylene (35) castor oil and polyoxyethylene (60) castor oil; the condensate of polyoxyethylene and hydrogenated castor oil is selected from polyoxyethylene (35) hydrogenated castor oil and polyoxyethylene (60) hydrogenated castor oil; the polysorbate is selected from polysorbate 60 and polysorbate 80; the phospholipid is selected from the group consisting of yolk lecithin, soybean lecithin, dipalmitoyl phosphatidylcholine, distearoyl phosphatidylcholine, and dimyristoyl phosphatidylcholine.

17. An essential oil extract from whole herbs including the seed-bearing spike of *Chenopodium ambrosioides L.*, wherein the extract comprises the following components by weight: α-terpinene 15-35%, p-cymene 15-25%, ascaridole 10-20% and α-terpinolene 32-40%, and the extract of *Chenopodium ambrosioides L.* is obtained by steam distillation as follows:

adding whole herbs including the seed-bearing spike of *Chenopodium ambrosioides L.* to a distillatory kettle;
 applying steam to a collector to pass over the whole herbs including the seed-bearing spike of *Chenopodium ambrosioides L.* in the distillatory kettle;
 keeping the extraction temperature at 85-100° C.; and
 collecting the essential oil extract from the *Chenopodium ambrosioides L.*

18. The essential oil extract of *Chenopodium ambrosioides L.* according to claim 17, wherein the extract comprises the following components by weight: α-terpinene 20-30%, p-cymene 18-22%, ascaridole 12-18% and α-terpinolene 32-35%.

19. The essential oil extract of *Chenopodium ambrosioides L.* according to claim 17, wherein the extract further comprises the following components by weight: γ-terpinene 0.5-0.7%, and/or limonene 0.6-0.8%.

20. The essential oil extract of *Chenopodium ambrosioides L.* according to claim 18, wherein the extract further comprises the following components by weight: γ-terpinene 0.5-0.7%, and/or limonene 0.6-0.8%.

\* \* \* \* \*